(12) United States Patent
Lin et al.

(10) Patent No.: US 8,007,647 B2
(45) Date of Patent: Aug. 30, 2011

(54) RETENTION OF COUNTERIONS IN THE SEPARATIVE BIOREACTOR

(75) Inventors: YuPo J. Lin, Naperville, IL (US); Seth W. Snyder, Lincolnwood, IL (US); Edward J. St. Martin, Libertyville, IL (US)

(73) Assignee: UChicago Argonne, LLC, Chicago, IL (US)

( * ) Notice: Subject to any disclaimer, the term of this patent is extended or adjusted under 35 U.S.C. 154(b) by 523 days.

(21) Appl. No.: 12/005,586

(22) Filed: Dec. 27, 2007

(65) Prior Publication Data

US 2008/0187902 A1    Aug. 7, 2008

Related U.S. Application Data

(63) Continuation of application No. 10/993,642, filed on Nov. 19, 2004, now abandoned.

(51) Int. Cl.
*B01D 61/48* (2006.01)

(52) U.S. Cl. .......................... 204/536; 204/632

(58) Field of Classification Search .................. 204/524, 204/530, 533, 632, 536
See application file for complete search history.

(56) References Cited

U.S. PATENT DOCUMENTS

| | | | |
|---|---|---|---|
| 3,767,548 A * | 10/1973 | Okada et al. | 426/239 |
| 5,980,961 A * | 11/1999 | Berrocal et al. | 426/239 |
| 6,495,014 B1 | 12/2002 | Datta et al. | |
| 6,797,140 B2 | 9/2004 | Lin et al. | |
| 2004/0115783 A1 | 6/2004 | Arora et al. | |

* cited by examiner

*Primary Examiner* — Arun S Phasge
(74) *Attorney, Agent, or Firm* — Olson & Cepuritis, Ltd.

(57) ABSTRACT

A bioreactor with an anode and a cathode, and a plurality of reaction chambers each having an inlet and an outlet and each including a porous solid ion exchange wafer having ion-exchange resins. Each of the reaction chambers is interleaved between a cation exchange membrane and an anion exchange membrane or between either a cation or an anion exchange membrane and a bipolar exchange membrane. A product chamber is separated from one of the reaction chambers by either a cation or an anion exchange membrane. Recirculation mechanism is provided for transporting material between the reaction chamber inlets and outlets. A method of producing organic acids, amino acids, or amines using the separative bioreactor is disclosed.

25 Claims, 4 Drawing Sheets

RETENTION OF COUNTERIONS IN THE SEPARATIVE BIOREACTOR

RELATED APPLICATIONS

This application, pursuant to 37 C.F.R. 1.78(c), claims priority based on provisional application Ser. No. 60/612,849 filed on Sep. 24, 2004 and application Ser. No. 10/993,642 filed Nov. 19, 2004.

CONTRACTUAL ORIGIN OF THE INVENTION

The United States Government has rights in this invention pursuant to Contract No. W-31-109-ENG-38 between the United States Government and The University of Chicago and/or pursuant to Contract No. DE-AC02-06CH11357 between the United States Government and UChicago Argonne, LLC representing Argonne National Laboratory.

BACKGROUND OF THE INVENTION

This invention relates to the use of a separative bioreactor for treating fluids via electrodeionization (EDI) and more particularly, to the production of organic acids, amino acids, or amines by fermentation and/or enzymatic processes.

Electrodeionization, also known as electrochemical ion-exchange, is an advanced ion-exchange technology that combines the advantages of ion-exchange and electrodialysis. In an electrodeionization process, ion exchange resins are sequestered in dilute compartments to increase ionic conductivity, so that even with very dilute ionic feed ($10^{-5}$N), a stable operation with higher flux and lower energy consumption than electrodialysis becomes possible. EDI technology is presently used to make deionized water for boiler feed and high purity and industrial water applications. However, there are also other uses and potential uses of such technology for processing organic streams in a variety of industries. Some of these technologies have been touched on by patent applications and/or issued patents filed on behalf of Argonne National Laboratory (ANL) such as U.S. Pat. No. 6,797,140 issued Sep. 28, 2004 and U.S. Ser. No. 10/702,798 filed Nov. 5, 2003 and U.S. Pat. No. 6,495,014 issued Dec. 17, 2003, the entire disclosures of each of these references being herein incorporated by reference.

In many fermentation and enzymatic processes, it is frequently required to maintain a high (milimolar) concentration of medium components. Common examples are mono and divalent cations and anions that provide an appropriate required ionic environment for optimum activity of microorganisms and enzymes. These mono and divalent cations and anions are identified as counterions hereinafter and the concentrations of them in the reaction medium should be maintained within a predetermined range to ensure optimum reaction conditions. During the direct capture of ionic products such as organic acids, amino acids and amines and an EDI driven separative bioreactor device, sometimes important ionic species such as counterions are separated from the fermentation broth or reaction medium. It is this loss of counterion concentration in the fermentation broth or reaction medium that is a serious problem in the art because replacement of the counterions in a flow through system would be expensive and prohibitively increase the cost of obtaining the product.

SUMMARY OF THE INVENTION

Accordingly, it is an important object of the present invention to provide an apparatus and method to maintain the appropriate counterion concentration in the fermentation broth or reaction medium during continuous operation of a separative bioreactor.

Another object of the present invention is to provide a separative bioreactor, comprising an anode and a cathode, a plurality of reaction chambers each having an inlet and an outlet and each including a porous solid ion exchange wafer having ion-exchange resins, each of the reaction chambers being interleaved between a cation exchange membrane and an anion exchange membrane or between either a cation or an anion exchange membrane and a bipolar exchange membrane, a plurality of product chambers each having an inlet and an outlet and separated from one of the reaction chambers by either a cation or an anion exchange membrane, recirculation mechanism for transporting material between the reaction chamber inlets and outlets and for transporting product between the product chamber inlets and outlets, and mechanism for supplying an electric potential between the anode and the cathode causing ions to be transported between chambers, whereby counterions retained or produced in each of the reaction chambers during the production of an ionizable organic product including product ions combine with oppositely charged ions to form molecules some or all of which are transported to reaction chamber inlets while product ions are transported into an adjacent product chamber to combine with oppositely charged ions to form product in a product stream exiting the product chamber outlets continuously recirculated to the product chamber inlets to increase the concentration of product in the product stream.

A still further object of the present invention is to provide a separative bioreactor, comprising an anode and a cathode, a plurality of reaction chambers each having an inlet and an outlet and each including a porous solid ion exchange wafer having ion-exchange resins, each of the reaction chambers being interleaved between a cation exchange membrane and an anion exchange membrane, a plurality of product chambers each having an inlet and an outlet and each separated from one of the reaction chambers by either a cation or an anion exchange membrane and a bipolar membrane, a plurality of counterion chambers each separated from an adjacent reaction chamber by either a cation or an anion exchange membrane, each of the reaction chambers being positioned between a product chamber and a counterion chamber, recirculation mechanism for transporting material between the reaction chamber inlets and outlets and for transporting product between the product chamber inlets and outlets and for transporting material between the counterion chamber inlets and outlets, and mechanism for supplying an electric potential between the anode and the cathode causing ions to be transported between chambers, whereby counterions retained or produced in the reaction chambers during the production of an ionizable organic product including product ions combine with oppositely charged ions to form molecules some or all of which are transported to a reaction chamber while product ions are transported into an adjacent product chamber to combine with oppositely charged ions to form product in a product stream exiting the product chamber outlets continuously recirculated to the product chamber inlets to increase the concentration of the product in the product stream.

Yet another object of the present invention is to provide a separative bioreactor, comprising an anode and a cathode, a plurality of reaction chambers each having an inlet and an outlet and each including a porous solid ion exchange wafer having ion-exchange resins, each of the reaction chambers being interleaved between either a cation or an anion exchange membrane and a bipolar exchange membrane, a plurality of product chambers each having an inlet and an outlet and each separated from one of the reaction chambers by either a cation or an anion exchange membrane, recirculation mechanism for transporting material between the reaction chamber inlets and outlets and for transporting product between the product chamber inlets and outlets, and mechanism for supplying an electric potential between the anode and the cathode causing ions to be transported between chambers, whereby counterions retained or produced in the reaction chambers during the production of an ionizable organic product including product ions combine with oppositely charged ions to form molecules some or all of which are transported to a reaction chamber with product ions being transported into an adjacent product chamber to combine with oppositely charged ions to form product in a product stream exiting the product chamber outlets continuously recirculated to the product chamber inlets to increase the concentration of the product in the product stream.

A final object of the present invention it to provide a method of increasing the production of an organic acid, amino acid, or amine by electrodeionization during the biochemical reaction of bacteria or enzyme with a substrate by maintaining the concentration of counterions during the reaction, comprising providing a separative bioreactor with an anode and a cathode, a plurality of reaction chambers each having an inlet and an outlet and each including a porous solid ion exchange wafer having ion-exchange resins, each of the reaction chambers being interleaved between a cation exchange membrane and an anion exchange membrane or between either a cation or an anion exchange membrane and a bipolar exchange membrane, a plurality of product chambers each having an inlet and an outlet and separated from one of the reaction chambers by either a cation or an anion exchange membrane, recirculation mechanism for transporting material between the reaction chamber inlets and outlets and for transporting product between the product chamber inlets and outlets, and mechanism for supplying an electric potential between the anode and the cathode causing ions to be transported between chambers in an electrodeionization process, whereby counterions retained or produced in each of the reaction chambers during the production of an ionizable organic product including product ions combine with oppositely charged ions to form molecules some or all of which are transported to reaction chamber inlets while product ions are transported into an adjacent product chamber to combine with oppositely charged ions to form product in a product stream exiting the product chamber outlets continuously recirculated to the product chamber inlets to increase the concentration of product in the product stream.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

DETAILED DESCRIPTION OF THE PRESENT INVENTION

Figure 1:
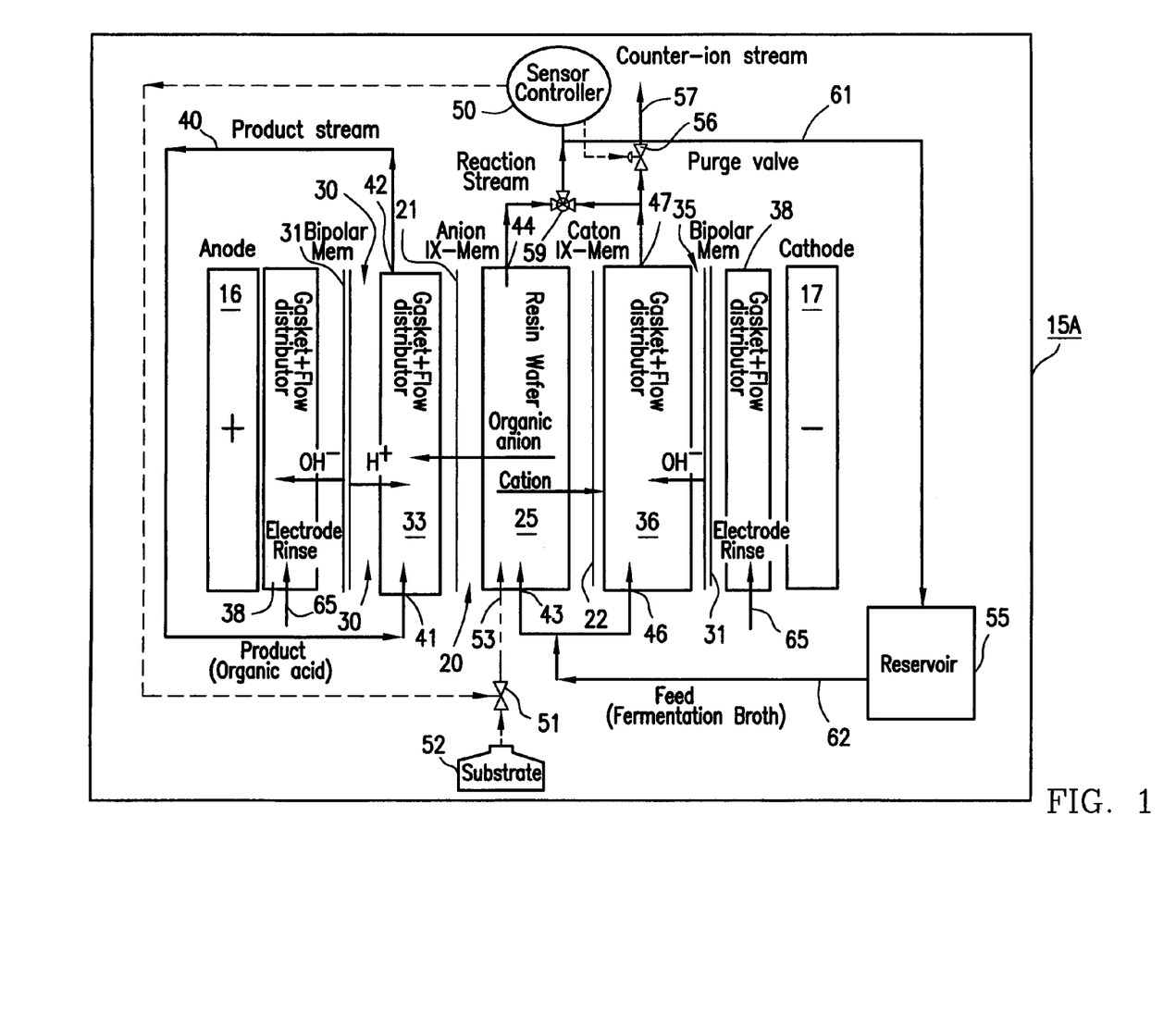
FIG. 1 is a schematic illustration of separative reactor for the capture of anion products and the recycle of cation counterions.
Figure 2:
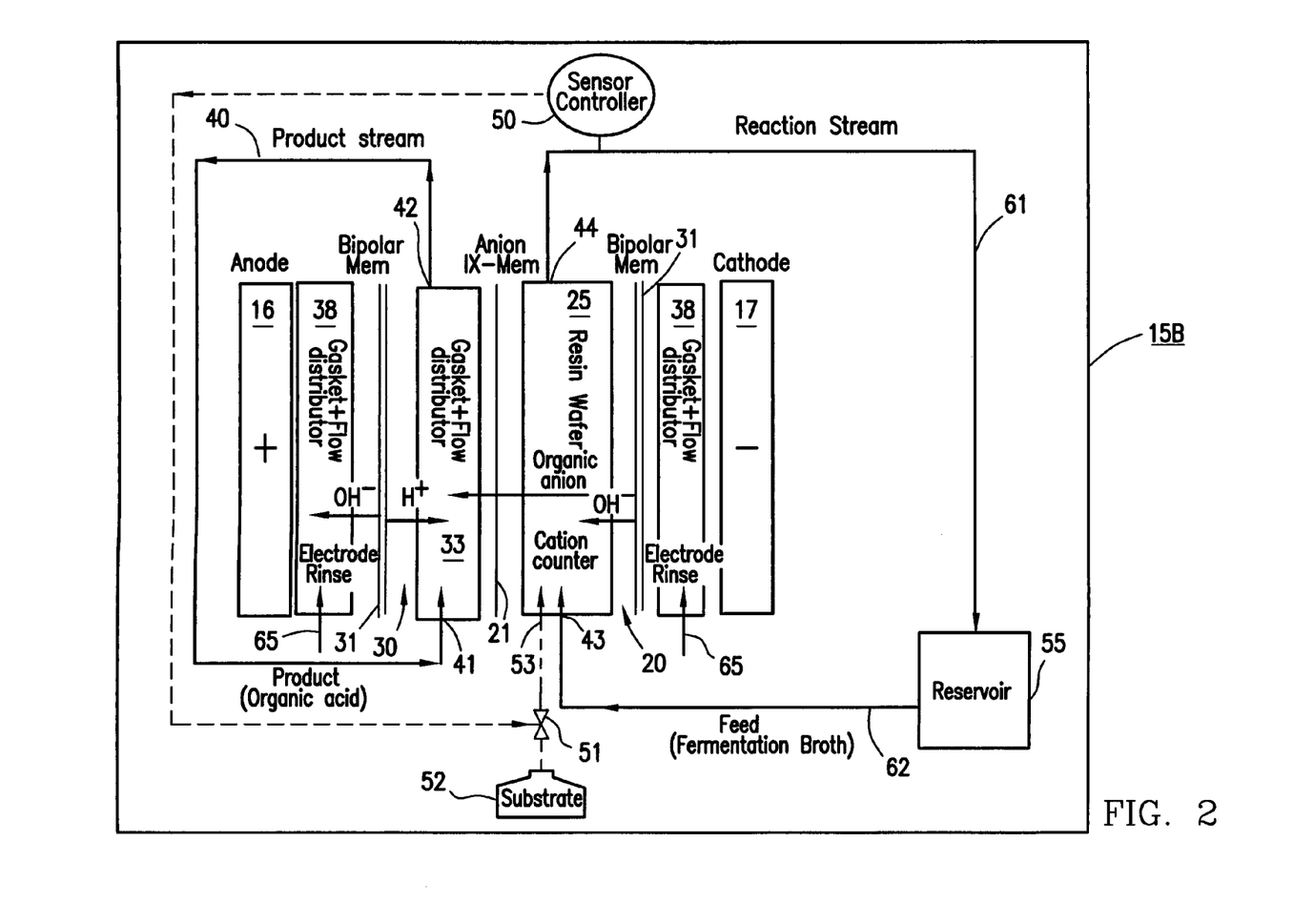
FIG. 2 is a schematic illustration of a 2-compartment EDI separative bioreactor; for the capture of cation counterions.
Figure 3:
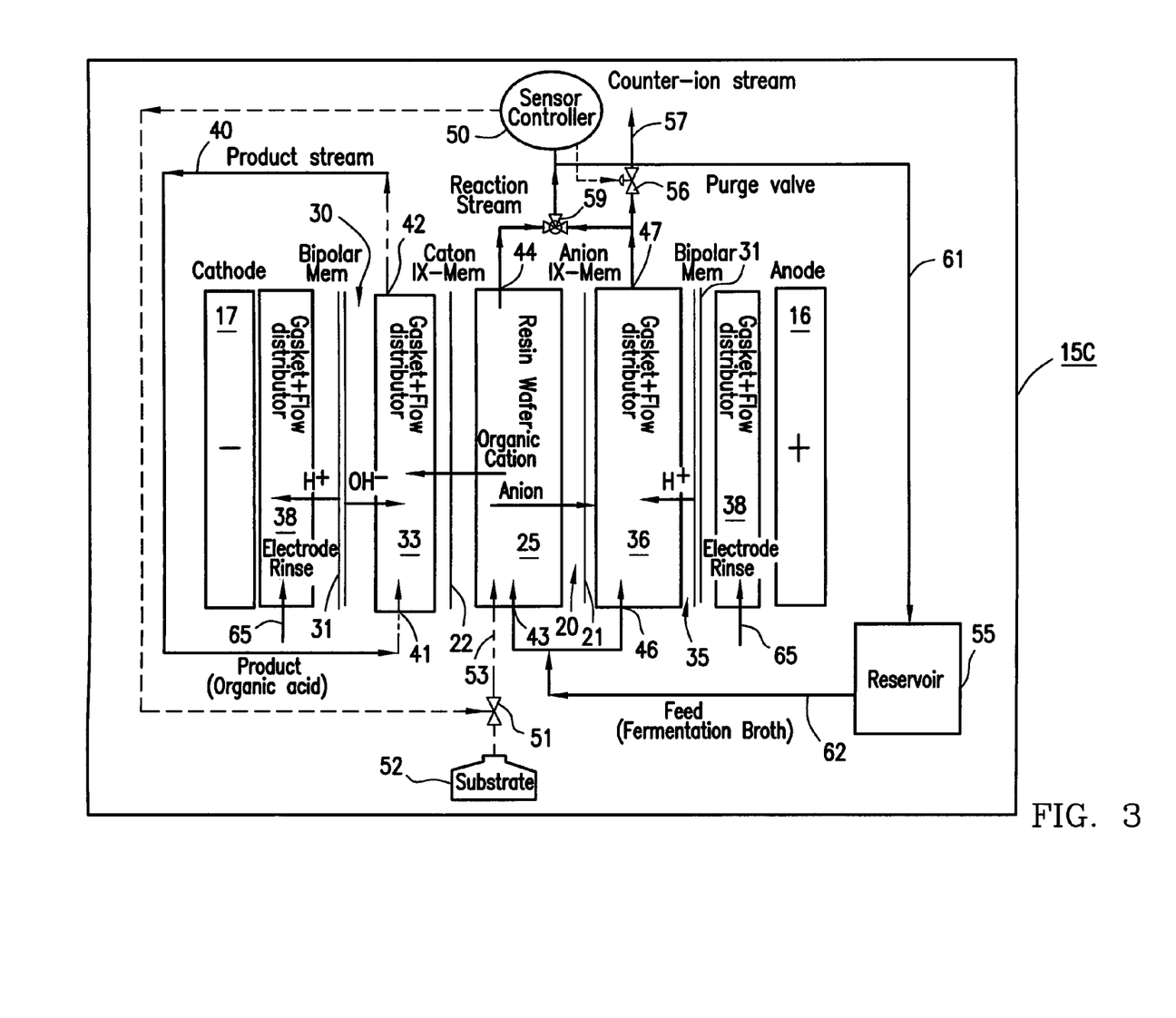
FIG. 3 is a schematic illustration of another 3-compartment EDI separative bioreactor for capture of cationic productions and recycle of anionic counterions.
Figure 4:
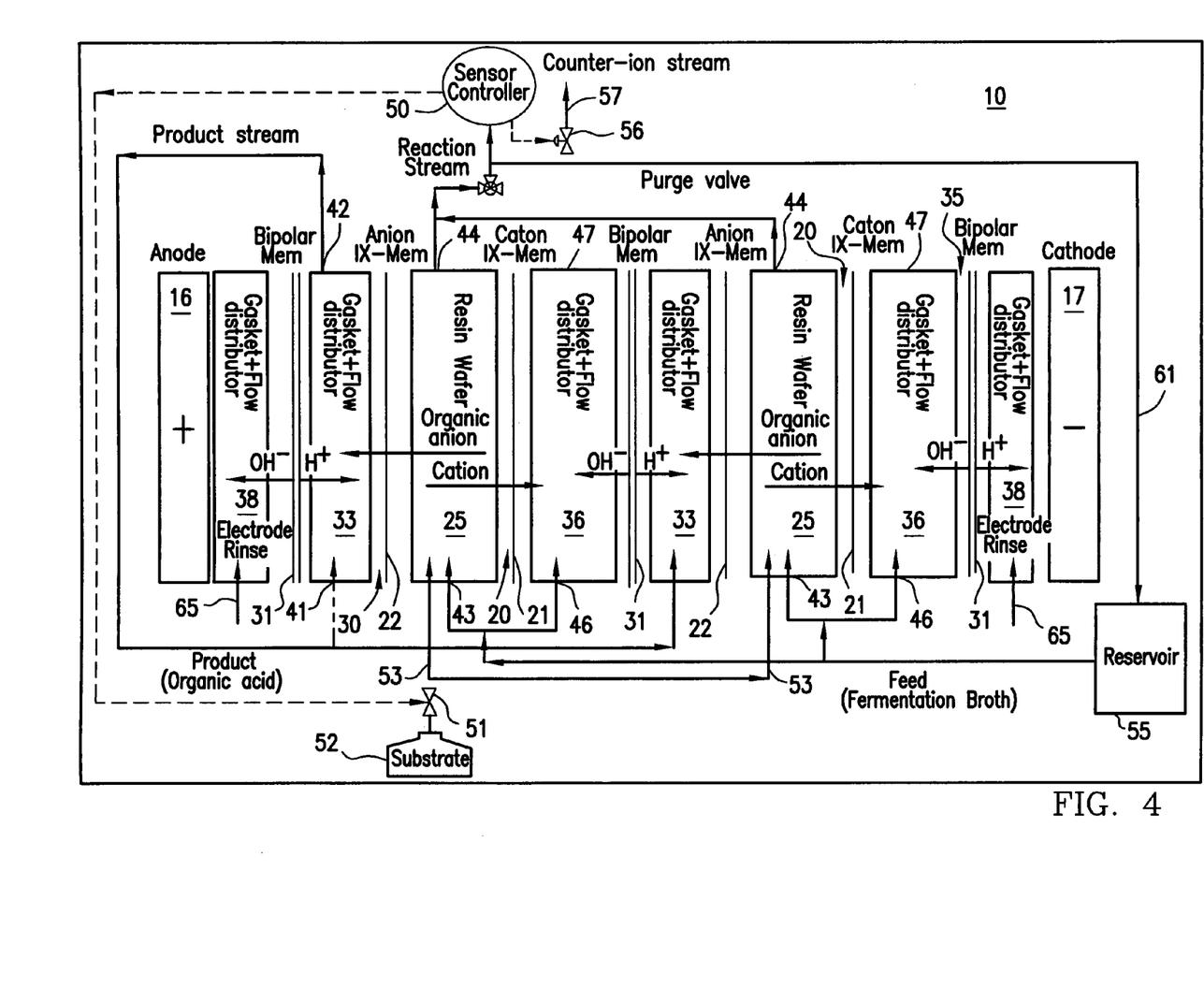
FIG. 4 is a schematic diagram of a 2-cell pair configuration of the 3-compartment EDI separative bioreactor for the capture of ionic products and recycle of cation counterions.

Referring to the drawings, there is illustrated in FIG. 4 a separative bioreactor or electrodeionization (EDI) stack 10 consisting of multiple cell pairs 15, representative cell pairs 15A, 15B and 15C are illustrated respectively in FIGS. 1-3.

Referring to the figures, there is seen that the separative bioreactor 10 is provided with an anode 16 and a cathode 17 intermediate which are the various cell pairs 15 of which only two are shown for illustration in FIG. 4, but may in commercial situations comprise a much larger number. However, as illustrated in FIG. 1, a three chamber or compartment EDI separative bioreactor 15A includes a reaction chamber 20 formed between an anion exchange membrane 21 and a cation exchange membrane 22, the reaction chamber 20 housing a resin wafer 25 of the type previously described in the above-identified and incorporated U.S. patent and patent applications. As indicated in the patent and patent applications, the resin wafer 25 is porous, preferably having a porosity in the range of between 15% to about 60% and contains one or more of anion exchange moieties or cation exchange moieties or mixtures thereof immobilized with respect to each other with a binder comprising from about 25% to about 45% by weight of the porous ion exchange material without substantially coating the moieties. Most preferably, each of the porous resin wafers 25 has a porosity of at least 15% and the binder is preferably present in a weight ratio to the moieties of about 1:3. As previously disclosed, the ion exchange resin wafers contain one or more of a strong acid resin, a weak acid resin, a strong basic resin or a weak basic resin and the ion exchange resins are preferably present in the range of from about 30% to about 80% by weight of the wafers 25 and most preferably in the range of about 55% to about 70% by weight of the wafers.

Each of the cell pairs 15 also contain a product chamber 30 formed by a bipolar membrane 31 and the anion exchange membrane 21. The product chamber 30 has therein a gasket and flow distributor device 33. A counterion chamber 35 is formed by a bipolar membrane 31 and a cation exchange membrane 22 and has therewithin a gasket and flow distributor 36. As is well known, a compartment for an electrode rinse gasket 38 and flow distributor is positioned intermediate each of the electrodes, that is the anode 16 and cathode 17, and the adjacent bipolar membrane 31.

The gasket and flow distributor 33, outlet 42 and inlet 41 provide a recycle loop of product, as will be described, produced with ions passing from the reaction chamber 20 through the anion exchange membrane 21. A reaction chamber inlet 43 and reaction chamber outlet 44 provide a flow path for material flowing through the resin wafer 25. The gasket and flow distributor 36 from within the counterion chamber 35 is provided with an inlet 46 and an outlet 47.

A sensor controller 50 is electronically in communication with a substrate source or supply 52 and controls a valve 51 intermediate the substrate source 52 and the substrate inlet 53. A purge valve 56 is located in the outlet 47 of the gasket and flow distributor 36 in the counterion chamber 35 and is electrically controlled by the sensor controller 50. A purge line 57 is in communication with the valve 56 and serves, as will be described, to purge excess counterions from the system. A valve 59 is intermediate the reaction chamber outlet 44 and the counterion outlet 47 and is in communication with the sensor controller 50. A line 61 provides communication between the valve 59 and hence the reaction chamber outlet 44 and the counterion chamber outlet 47 and a reservoir 55 which receives, as will be described, fermentation broth or reaction medium, and a line 62 provides communication between a reservoir 55 and the inlet 43 to the reaction chamber 20 and inlet 46 to the counterion chamber 35. Finally, an electrode rinse inlet 65 is provided for a purpose hereinafter described.

As noted, the difference between the cell pair illustrated in FIGS. 1 and 3 is the different position of the anion exchange membrane 21 and cation exchange membrane 22 with respect to the reaction chamber 20 permitting anions to flow into the product chamber 30 in FIG. 1 and cations flowing into chamber 30 in FIG. 3. Otherwise, FIGS. 1 and 3 are the same and like numbers are used to identify like parts in each figure. FIG. 2 illustrates a 2-compartment separate bioreactor in which a counterion chamber is missing and the reaction chamber 20 is separated from the product chamber 30 by either an ion exchange membrane 21 or a cation exchange membrane 22 thereby to provide anion flow into the product chamber in the first case and cation flow under the product chamber in the second case. In other respects, FIG. 2 is similar to FIG. 1 and like numbers have been used to identify to like parts.

The inventive design utilizes a three-compartment EDI separative bioreactor system. Referring to FIG. 1, a schematic of the bioreactor 10 for retaining counterions (in this example, cations) is shown. An ion exchange resin wafer 25 is in the reaction compartment 20 where the biological reaction takes place. The fermentation broth or reaction medium from a reservoir 55 is "proportionally" fed into the reaction and counterion stream compartments. The substrate is introduced into and merges with the reaction stream that enters the reaction compartment 20, through inlet 43. The amount of substrate injected is controlled through sensor 50 and valve 51 such that it would be largely consumed as the fluid passes through the reaction compartment 20. During the operation of the bioreactor 10, the applied current removes the desired organic anion (or cation) product into the product compartment. For electroneutrality, the cation (or anion) counterions in the reaction compartment 20 are stoichiometrically removed into the counterion compartment 35. The counterions are returned to the fermentation/reaction medium compartment 20 by recombining the reaction and counterion streams in the reservoir 55. In an alternative configuration, the three-compartment cell stack for counterion retention of FIG. 3 can be substituted with a two-compartment cell stack shown in FIG. 2. In this configuration, the counterions never leave the reaction chamber 20 and do not need to by recycled. In cases where the bipolar membrane 31 is fouled by the reaction media, separation efficiency would be reduced and the three-compartment cell configuration of FIGS. 1, 3, 4 are preferred. Both the two-compartment and three-compartment cell stacks of FIGS. 1, 2 and 3) capture anionic products and retain or recycle cations or 2) capture cationic products and retain or recycle anions. Ionizable products that are uncharged at pH 7 may be captured by adjusting the pH of the system above or below the pK of the desired product.

The captured molecules are preferable organic acids with between 2 and 6 carbons including: acetic, propionic, 3-hydroxypropionic, lactic, succinic, butyric, citric, gluconic and ascorbic acids. The capture molecules preferably are amino acids including lysine, glutamic acid, aspartic acid, asparagine, glutamine, histidine, arginine and others well known to a person of ordinary skill in this art.

EXAMPLES

1. Counter Cation Retention in a Separative Bioreactor for Lactic Acid Production A 3-compartment electrochemical stack is assembled in a separative bioreactor as shown schematically in FIG. 1. This stack has two cell pairs with 10 cm$^2$ cross-sectional area for current flow. The anion-exchange membrane, AH1, cation-exchange membrane, C6610F, and bipolar membrane were obtained from Ameridia Inc. Wafers with a mixture of cation and anion resins were used in the feed compartment. The mixing ratio was in the range of 25% to 75% anion exchange resin bead with the balance being cation resin beads PFC100E and PFA444 ion-exchange beads obtained from Purolite were used in the wafers. Porous wafers without ion-exchange resins were used for the counterion compartment. Initially, 2 g/L of lactic acid and 1 g/L of MgCl$_2$ was in the feed tank to simulate the lactic acid production. The product tank had an initial concentration of 0.1 g/L of lactic acid.

TABLE 1

Di-valent cation counter species retention during lactic acid separation

| Time (hour) | Product Lactic acid normalized (g/L) | Feed Lactic acid normalized (g/L) | Product* Mg$^{+2}$ (mg/L) | Feed pH | Product pH | Product Separation Efficiency |
|---|---|---|---|---|---|---|
| 0.0 | 0.10 | 1.69 | 0.340 | 2.30 | 3.17 | |
| 1.7 | 0.36 | 1.50 | 0.310 | 2.79 | 2.11 | 11% |
| 3.7 | 1.08 | 1.29 | 0.280 | 3.13 | 1.72 | 23% |
| 4.9 | 1.61 | 1.05 | 0.250 | 3.27 | 1.60 | 37% |
| 6.4 | 2.11 | 0.94 | 0.260 | 3.42 | 1.47 | 43% |
| 21.3 | 3.47 | 0.63 | 0.400 | 3.97 | 1.30 | 61% |

TABLE 2

Mono-valent cation counter species retention during glutamic acid separation

| Time | Product Glurtamic acid (normalized) | Feed Gluta. Acid normalized | Product* Na+ | Feed pH | Product pH | Product Separation Efficiency |
|---|---|---|---|---|---|---|
| 0.0 | 0.5 | 5.0 | 60 | 6.85 | 5.78 | |
| 1.0 | 1.5 | 4.1 | 70 | 8.20 | 3.00 | 17.8% |
| 2.8 | 4.4 | 3.3 | 75 | 9.15 | 2.78 | 33.0% |
| 5.5 | 8.6 | 2.4 | 100 | 9.89 | 2.83 | 50.1% |
| 7.3 | 11.3 | 1.9 | 113 | 10.57 | 2.89 | 60.8% |
| 24.2 | 15.5 | 0.5 | 120 | 12.05 | 3.29 | 87.2% |

*Initial concentration of Na+ in the feed is 615 mg/L

TABLE 3

Monovalent anion counterion retention during lysine (amino acid) separation

| Time | Product lysine normalized | Feed HCl-lysine normalized | Product* Cl$^-$ | Feed pH | Product pH | Product Separation |
|---|---|---|---|---|---|---|
| 0.0 | 0.348 | 4.580 | 90.0 | 5.50 | 6.00 | |
| 1.2 | 0.489 | 4.439 | 92.0 | 3.03 | 10.50 | 3% |
| 3.0 | 1.774 | 4.145 | 101.0 | 2.72 | 10.65 | 9% |
| 5.2 | 3.179 | 3.759 | 110.0 | 2.49 | 10.61 | 18% |
| 6.8 | 4.624 | 3.526 | 120.0 | 2.31 | 10.61 | 23% |
| 23.3 | 12.920 | 2.123 | 165.0 | 1.96 | 10.56 | 54% |

*Initial concentration of Cl$^-$ in the feed is 972 mg/L

Table 1 shows the results after 21 hours of continuous operation. 60% of the lactic acid was removed from the feed compartment (i.e., the reactor). The concentration of the cation counter species, $Mg^{+2}$, was maintained near 1 g/L in the feed compartment and only traces of $Mg^{+2}$ (less than 0.4 mg/L) was found in the product compartment. This means that less than 0.02% of the $Mg^{+2}$ in the feed stream was transported into the product stream after 21 hours of operation.

2. Counter Cation Retention in the Separative Bioreactor for Glutamic Acid Production The same stack assembly as described in Example 1 was used. During the experiment, the feed tank initially contained 1 L of 5 g/L mono-sodium glutamate. The product tank initially had 0.2 L of 0.5 g/L mono-sodium glutamate. The results are shown in Table 2. By controlling the ratio of cation/anion in the wafer, the pH of the feed stream was controlled in the basic range that is above the $pK_3$ value. The reactor achieved high separation efficiency for glutamic acid. Within 7 hours, the separation efficiency reached 60%. The final product separation reached nearly 90% after 24 hours of operation. The average separation rate was around 140 g/m²/hour. The concentration of the cation counterion, $Na^+$, transported to the product compartment was less than 1% after 24 hours of operation. This provides an example for amino acid production and capture while retaining counterions when using the new separative bioreactor design.

3. Counter Anion Retention in the Separative Bioreactor for Lysine Production

In this example, the electrochemical stack was assembled according to the schematic shown in FIG. 3. The wafer and ion-exchange membranes used in the experiment are the same as described in Example 1. 1 L of 5 g/L of mono-HCl lysine and 0.2 L of 0.5 g/L lysine HCl solutions were prepared initially in the feed and product tanks, respectively. The pH of the feed compartment was controlled in-situ in the acidic range. After 23.5 hours of operation, 55% of the lysine was separated from the feed while the majority of anion counterion, $Cl^-$, remained in the feed tank. Only 0.7% of the $Cl^-$-ion in the feed stream was transported into the product stream after 23.5 hours of operation.

In order to maintain the concentration of counterion species, such as essential nutrients, in a separative bioreactor 10, different three-compartments electrodeionization cell stacks with different arrangements of ion-exchange membranes 21, 22 and 31 were constructed and tested. 99% of the counterion species in the bioreactor reservoir 55 (i.e., the feed tank) remained in the feed stream while the organic acids were been separated. This demonstrates the effectiveness of the subject invention.

While particular embodiments of the present invention have been shown and described, it will be appreciated by those skilled in the art that changes, modifications and improvements may be made, for example in the processing of the materials or in the electrode and/or cell design without departing from the true spirit and scope of the invention.

The embodiments of the invention in which an exclusive property or privilege is claimed are defined as follows:

1. A separative bioreactor comprising:
   (a) an anode and a cathode,
   (b) a plurality of reaction chambers each having an inlet and an outlet and each including a porous solid ion exchange wafer having ion-exchange resins, each of the reaction chambers being interleaved between either (i) a cation exchange membrane and a bipolar membrane or (ii) an anion exchange membrane and a bipolar exchange membrane,
   (c) a plurality of product chambers each having an inlet and an outlet and separated from one of the reaction chambers by either a cation or an anion exchange membrane,
   (d) recirculation mechanism for transporting material between the reaction chamber inlets and outlets and for transporting product between the product chamber inlets and outlets, and
   (e) mechanism for supplying an electric potential between the anode and the cathode causing ions to be transported between chambers, whereby counterions retained or produced in each of the reaction chambers during the production of an ionizable organic product including product ions combine with oppositely charged ions to form molecules some or all of which are transported by said recirculation mechanism to reaction chamber inlets while product ions are transported into an adjacent product chamber to combine with oppositely charged ions to form product in a product stream exiting the product chamber outlets continuously recirculated to the product chamber inlets to increase the concentration of product in the product stream; wherein bipolar membranes are positioned intermediate each anode or cathode and the adjacent chamber.

2. The separative bioreactor of claim 1, wherein said ion-exchange resins are present in the range of from about 30% to about 80% by weight of said wafers.

3. The separative bioreactor of claim 1, wherein said ion-exchange resins are present in the range of from about 55% to about 70% by weight of said wafers.

4. The separative bioreactor of claim 1, wherein said wafers are flexible porous ion-exchange material containing one or more of anion-exchange moieties or cation-exchange moieties or mixtures thereof immobilized with respect to each other with a binder comprising from about 25% to about 45% by weight of said porous ion-exchange material without substantially coating the moieties.

5. The separative bioreactor of claim 4, wherein said porous wafers have at least 15% porosity and the binder is present in a weight ratio to the moieties of about 1:3.

6. The separative bioreactor of claim 1, wherein each of said porous wafers has a porosity in the range of from about 15% to about 60%.

7. The separative bioreactor of claim 1, wherein said wafers contain one or more of a strong acid resin, a weak acid resin, a strong basic resin, or a weak basic resin.

8. The separative bioreactor of claim 1, wherein the molecules produced from the counterions are mixed with feed material during transport to said reaction chamber inlets.

9. The separative bioreactor of claim 1, and further including a source of substrate in communication with said reaction chamber inlets and a substrate sensor in communication with said reaction chamber outlets and valve mechanism in communication with said substrate sensor to control the amount of substrate entering said reaction chamber inlets in response to the amount of substrate present at said reaction chamber outlets.

10. The separative bioreactor of claim 1, and further including a conductivity sensor in communication with the counterions retained or produced in said reaction chamber and purge mechanism in communication with said conductivity sensor for removing counterions from said bioreactor to maintain the concentration of counterions therein within a predetermined range.

11. The separative bioreactor of claim 1, wherein the product is an organic acid, amino acid, or an amine.

12. A separative bioreactor comprising:
(a) an anode and a cathode,
(b) a plurality of reaction chambers each having an inlet and an outlet and each including a porous solid ion exchange wafer having ion-exchange resins, each of the reaction chambers being interleaved between either (i) a cation exchange membrane and a bipolar membrane or (ii) an anion exchange membrane and a bipolar membrane,
(c) a plurality of product chambers each having an inlet and an outlet and each separated from one of the reaction chambers by either (i) a cation exchange membrane and a bipolar membrane or (ii) an anion exchange membrane and a bipolar membrane,
(d) a plurality of counterion chambers each separated from an adjacent reaction chamber by either a cation or an anion exchange membrane, each of the reaction chambers being positioned between a product chamber and a counterion chamber,
(e) recirculation mechanism for transporting material between the reaction chamber inlets and outlets and for transporting product between the product chamber inlets and outlets and for transporting material between the counterion chamber inlets and outlets, and
(f) mechanism for supplying an electric potential between the anode and the cathode causing ions to be transported between chambers, whereby counterions retained or produced in the reaction chambers during the production of an ionizable organic product including product ions combine with oppositely charged ions to form molecules some or all of which are transported to a reaction chamber while product ions are transported into an adjacent product chamber to combine with oppositely charged ions to form product in a product stream exiting the product chamber outlets continuously recirculated to the product chamber inlets to increase the concentration of the product in the product stream; wherein bipolar membranes are positioned intermediate each anode or cathode and the adjacent chamber.

13. The separative bioreactor of claim 12, wherein said wafers contain one or more of a strong acid resin, a weak acid resin, a strong basic resin, or a weak basic resin present in the range of from about 55% to about 70% by weight of said wafers, said wafers having a porosity of not less than about 15% and a binder present in the range of from about 25% to about 45% by weight of said resins without substantially coating cation-exchange moieties or anion-exchange moieties present in said resins.

14. The separative bioreactor of claim 13, and further including a source of substrate in communication with said reaction chamber inlets and a substrate sensor in communication with said reaction chamber outlets and valve mechanism in communication with said substrate sensor to control the amount of substrate entering said reaction chamber inlets in response to the amount of substrate present at said reaction chamber outlets.

15. The separative bioreactor of claim 14, and further including a conductivity sensor in communication with the counterions produced in said reaction chamber and purge mechanism in communication with said conductivity sensor for removing counterions from said bioreactor to maintain the concentration of counterions therein within a predetermined range.

16. The separative bioreactor of claim 15, wherein the product is an organic acid, amino acid, or an amine.

17. A separative bioreactor comprising:
(a) an anode and a cathode,
(b) a plurality of reaction chambers each having an inlet and an outlet and each including a porous solid ion exchange wafer having ion-exchange resins, each of said reaction chambers being interleaved between either (i) a cation exchange membrane and a bipolar membrane or (ii) an anion exchange membrane and a bipolar exchange membrane,
(c) a plurality of product chambers each having an inlet and an outlet and each separated from one of said reaction chambers by either a cation or an anion exchange membrane,
(d) recirculation mechanism for transporting material between said reaction chamber inlets and outlets and for transporting product between said product chamber inlets and outlets, and
(e) mechanism for supplying an electric potential between the anode and the cathode causing ions to be transported between chambers, whereby counterions retained or produced in said reaction chambers during the production of an ionizable organic product including product ions combine with oppositely charged ions to form molecules some or all of which are transported to a reaction chamber with product ions being transported into an adjacent product chamber to combine with oppositely charged ions to form product in a product stream exiting said product chamber outlets continuously recirculated to said product chamber inlets to increase the concentration of the product in the product stream; wherein bipolar membranes are positioned intermediate each anode or cathode and the adjacent chamber.

18. The separative bioreactor of claim 17, wherein said wafers contain one or more of a strong acid resin, a weak acid resin, a strong basic resin, or a weak basic resin present in the range of from about 55% to about 70% by weight of said wafers, said wafers having a porosity of not less than about 15% and a binder present in the range of from about 25% to about 45% by weight of said resins without substantially coating cation-exchange moieties or anion-exchange moieties present in said resins.

19. The separative bioreactor of claim 18, and further including a source of substrate in communication with said reaction chamber inlets and a substrate sensor in communication with said reaction chamber outlets and valve mechanism in communication with said substrate sensor to control the amount of substrate entering said reaction chamber inlets in response to the amount of substrate present at said reaction chamber outlets.

20. The separative bioreactor of claim 19, wherein the product is an organic acid, amino acid, or an amine.

21. A method of increasing the production of an organic acid, amino acid, or amine by electrodeionization during the biochemical reaction of bacteria or enzyme with a substrate by maintaining the concentration of counterions during the reaction, the method comprising reacting a substrate which is a precursor of an organic acid, an amino acid, or an amine with a bacteria or an enzyme in a separative bioreactor comprising:
(a) an anode and a cathode,
(b) a plurality of reaction chambers each having an inlet and an outlet and each including a porous solid ion exchange wafer having ion-exchange resins, each of said reaction chambers being interleaved between either (i) a cation exchange membrane and a bipolar membrane or (ii) an anion exchange membrane and a bipolar exchange membrane, (c) a plurality of product chambers each having an inlet and an outlet and separated from one of said reaction chambers by either a cation or an anion exchange membrane, (d) recirculation mechanism for transporting material between said reaction chamber inlets and outlets and for transporting product between said product chamber inlets and outlets, and (e) mechanism for supplying an electric potential between the anode and the cathode causing ions to be transported between chambers in an electrodeionization process, whereby counterions retained or produced in each of said reaction chambers during the production of an ionizable organic product including product ions combine with oppositely charged ions to form molecules some or all of which are transported to reaction chamber inlets while product ions are transported into an adjacent product chamber to combine with oppositely charged ions to form product in a product stream exiting said product chamber outlets continuously recirculated to said product chamber inlets to increase the concentration of product in the product stream; wherein bipolar membranes are positioned intermediate each anode or cathode and the adjacent chamber.

22. The method of claim 21, wherein said wafers contain one or more of a strong acid resin, a weak acid resin, a strong basic resin, or a weak basic resin present in the range of from about 55% to about 70% by weight of said wafers, said wafers having a porosity of not less than about 15% and a binder present in the range of from about 25% to about 45% by weight of said resins without substantially coating cation-exchange moieties or anion-exchange moieties present in said resins.

23. The method of claim 22, and further including providing a source of substrate in communication with said reaction chamber inlets and a substrate sensor in communication with said reaction chamber outlets and valve mechanism in communication with said substrate sensor to control the amount of substrate entering said reaction chamber inlets in response to the amount of substrate present at said reaction chamber outlets.

24. The method of claim 23, and further providing a conductivity sensor in communication with the counterions produced in said reaction chamber and purge mechanism in communication with said conductivity sensor for removing counterions from said bioreactor to maintain the concentration of counterions therein within a predetermined range.

25. The method of claim 24, wherein the organic acid is one or more of acetic, propionic, 3-hydroxypropionic, lactic, succinic, butyric, citric, gluconic and ascorbic acids and the organic amine is one or more of lysine, glutamic acid, aspartic acid, asparagine, glutamine, histidine, or arginine.

* * * * *